(12) United States Patent
Benam et al.

(10) Patent No.: US 11,679,546 B2
(45) Date of Patent: Jun. 20, 2023

(54) BIOPRINTER AND METHODS OF MANUFACTURING AN ORGANOMIMETIC DEVICE

(71) Applicant: THE REGENTS OF THE UNIVERSITY OF COLORADO, A BODY CORPORATE, Denver, CO (US)

(72) Inventors: Kambez Benam, Denver, CO (US); Alexander Kaiser, Keenesburg, CO (US)

(73) Assignee: The Regents Of The University Of Colorado, A Body Corporate, Denver, CO (US)

( * ) Notice: Subject to any disclaimer, the term of this patent is extended or adjusted under 35 U.S.C. 154(b) by 87 days.

(21) Appl. No.: 16/967,395

(22) PCT Filed: Feb. 11, 2019

(86) PCT No.: PCT/US2019/017540
§ 371 (c)(1),
(2) Date: Aug. 4, 2020

(87) PCT Pub. No.: WO2019/157464
PCT Pub. Date: Aug. 15, 2019

(65) Prior Publication Data
US 2021/0213673 A1 Jul. 15, 2021

Related U.S. Application Data

(60) Provisional application No. 62/628,727, filed on Feb. 9, 2018.

(51) Int. Cl.
*B29C 64/106* (2017.01)
*B33Y 10/00* (2015.01)
(Continued)

(52) U.S. Cl.
CPC .......... *B29C 64/106* (2017.08); *B29C 64/209* (2017.08); *B29C 64/232* (2017.08);
(Continued)

(58) Field of Classification Search
CPC ... B29C 64/106; B29C 64/232; B29C 64/245; B29C 64/209; B29C 64/393;
(Continued)

(56) References Cited

U.S. PATENT DOCUMENTS 4,649,911 A 3/1987 Knight et al.
8,281,641 B1 10/2012 Wooten et al.
(Continued)

FOREIGN PATENT DOCUMENTS

CN 106635954 5/2017
WO 2007119073 10/2007
(Continued)

OTHER PUBLICATIONS

International Search Report and Written Opinion dated Apr. 15, 2019 in Application No. PCT/US2019/017540.
(Continued)

*Primary Examiner* — Joseph S Del Sole
*Assistant Examiner* — Lawrence D. Hohenbrink, Jr.
(74) *Attorney, Agent, or Firm* — Snell & Wilmer, L.L.P.

(57) ABSTRACT

A bioprinter for manufacturing an organomimetic device includes at least one extruder configured to extrude a material, a three-dimensional movement assembly, and a build-plate mounted to the three-dimensional movement assembly. The build-plate may be configured to support the organomimetic device being manufactured. The bioprinter may further include a controller operably coupled to and configured to control the at least one extruder, the three-dimen-
(Continued)

sional movement assembly, and the build-plate. The at least one extruder may be non-movably fixed to the cabinet.

17 Claims, 6 Drawing Sheets

(51) Int. Cl.

| | |
|---|---|
| *B33Y 30/00* | (2015.01) |
| *B33Y 50/02* | (2015.01) |
| *B33Y 70/00* | (2020.01) |
| *B29C 64/232* | (2017.01) |
| *B29C 64/245* | (2017.01) |
| *B29C 64/209* | (2017.01) |
| *B29C 64/393* | (2017.01) |
| *B29C 64/236* | (2017.01) |
| *C12M 3/00* | (2006.01) |
| *C12M 1/26* | (2006.01) |
| *B29L 31/00* | (2006.01) |

(52) U.S. Cl.
CPC .......... *B29C 64/236* (2017.08); *B29C 64/245* (2017.08); *B29C 64/393* (2017.08); *B33Y 10/00* (2014.12); *B33Y 30/00* (2014.12); *B33Y 50/02* (2014.12); *B33Y 70/00* (2014.12); *C12M 21/08* (2013.01); *C12M 33/00* (2013.01); *B29L 2031/753* (2013.01)

(58) Field of Classification Search
CPC ....... B29C 64/236; B33Y 10/00; B33Y 30/00; B33Y 50/02; B33Y 70/00; C12M 21/08; C12M 33/00; B29L 2031/753
USPC .......................................................... 264/308
See application file for complete search history.

(56) References Cited

U.S. PATENT DOCUMENTS

| | | | |
|---|---|---|---|
| 8,647,410 B2 | 2/2014 | Borenstein et al. | |
| 8,647,861 B2 | 2/2014 | Ingber et al. | |
| 11,001,005 B2* | 5/2021 | Cohen | B29C 64/364 |
| 2006/0156978 A1 | 7/2006 | Lipson et al. | |
| 2006/0195179 A1 | 8/2006 | Sun et al. | |
| 2011/0033887 A1 | 2/2011 | Fang et al. | |
| 2011/0086382 A1 | 4/2011 | Marx | |
| 2011/0250585 A1 | 10/2011 | Ingber et al. | |
| 2011/0250688 A1 | 10/2011 | Hasan | |
| 2014/0057311 A1 | 2/2014 | Kamm et al. | |
| 2014/0158233 A1 | 6/2014 | Leslie et al. | |
| 2014/0335496 A1 | 11/2014 | Grego et al. | |
| 2014/0342445 A1 | 11/2014 | Ingber et al. | |
| 2014/0352689 A1 | 12/2014 | Seshadri et al. | |
| 2015/0004077 A1 | 1/2015 | Wikswo et al. | |
| 2015/0240194 A1 | 8/2015 | Neumann et al. | |
| 2015/0377861 A1 | 12/2015 | Pant et al. | |
| 2016/0068793 A1* | 3/2016 | Maggiore | B29C 64/232 901/22 |
| 2016/0074558 A1* | 3/2016 | Murphy | C12M 33/00 425/135 |
| 2016/0167051 A1 | 6/2016 | Collins | |
| 2016/0288414 A1* | 10/2016 | Ozbolat | A61F 2/2875 |
| 2016/0313306 A1 | 10/2016 | Ingber et al. | |
| 2017/0198252 A1 | 7/2017 | Mironov et al. | |
| 2017/0210064 A1* | 7/2017 | Aw | B29C 48/29 |
| 2017/0355153 A1* | 12/2017 | Albert | B29C 64/255 |
| 2017/0355940 A1 | 12/2017 | Neumann et al. | |
| 2018/0085493 A1* | 3/2018 | Lee | D01D 5/0007 |
| 2018/0106784 A1 | 4/2018 | Sears et al. | |
| 2018/0110901 A1* | 4/2018 | Lewis | B33Y 80/00 |
| 2018/0326665 A1* | 11/2018 | Gatenholm | B29C 64/245 |
| 2019/0210283 A1* | 7/2019 | Rouse | B01L 9/02 |
| 2019/0375163 A1* | 12/2019 | Sternå | B33Y 70/00 |
| 2020/0197562 A1* | 6/2020 | Xue | C08G 63/664 |

FOREIGN PATENT DOCUMENTS

| | | |
|---|---|---|
| WO | 2012154834 | 11/2012 |
| WO | 2013086486 | 6/2013 |
| WO | 2013086502 | 6/2013 |
| WO | 2013155513 | 10/2013 |
| WO | 2015138034 | 9/2015 |
| WO | 2016164566 | 10/2016 |
| WO | 2016179242 | 11/2016 |
| WO | 2017019778 | 2/2017 |
| WO | 2017040675 | 3/2017 |

OTHER PUBLICATIONS

Ozbolat et al., "Bioprinting toward organ fabrication: challenges and future trends," IEEE Transactions on Biomedical Engineering, vol. 60, 3, pp. 691-699 (2013).
Bajaj et al. "3D biofabrication strategies fortissue engineering and regenerative medicine," Annual Review Biomed Engineering, pp. 247-276 (2014).
Landers et al., "Fabrication of soft tissue engineering scaffolds by means of rapid prototyping techniques," Journal of Materials Science, 37, pp. 3107-3116 (2002).
Melchels et al., "Additive manufacturing of tissues and organs," School of Engineering & Physical Sciences, Institute of Biological Chemistry, Biophysics and Bioengineering, vol. 37, pp. 1079-1104 (2012).
Gesim Bioinstruments and Microfluids, https://gesim-bioinstruments-microfluidics.com/. Accessed on: Aug. 4, 2020.
There's Only One 3D-Bioplotter. https://envisiontec.com/3d-printers/3d-bioplotter/. Accessed on: Aug. 4, 2020.
Bioprinter Fabion. https://bioprinting.ru/en/products-services/fabion/. Accessed on: Aug. 4, 2020.
Cyfuse Regenova. https://www.cyfusebio.com/en/product/3dprinter/device/. Accessed on: Aug. 4, 2020.
Cyfuse S-Pike. https://www.cyfusebio.com/en/product/3dprinter/spike/. Accessed on: Aug. 4, 2020.
Aspect Biosystems. https://www.aspectbiosystems.com/technology. Accessed on: Aug. 4, 2020.
BioAssemblybot. https://www.advancedsolutions.com/bioassemblybot. Accessed on: Aug. 4, 2020.
Organovo Technology Platform, https://organovo.com/technology-platform/. Accessed on: Aug. 4, 2020.
Regenhu Biosystem Architects—3DDiscovery Evolution, https://www.regenhu.com/3d-bioprinters. Accessed on Aug. 4, 2020.
BioBotBasic. https://www.advancedsolutions.com/biobot. Accessed on: Aug. 4, 2020.
Allevi—Compare Bioprinters, https://www.allevi3d.com/compare/. Accessed on: Aug. 4, 2020.
Aether, https://discoveraether.com/. Accessed on: Aug. 4, 2020.
Cellink Life Sciences, https://www.cellink.com/. Accessed on: Aug. 4, 2020.
International Preliminary Report on Patentability dated Aug. 11, 2020 in Application No. PCT/US2019/017540.
Non-Final Office Action dated Mar. 25, 2021 in U.S. Appl. No. 16/438,092.
Final Office Action dated Dec. 17, 2021 in U.S. Appl. No. 16/438,092.
Advisory Action dated Mar. 11, 2022 in U.S. Appl. No. 16/438,092.
Non-Final Office Action dated Oct. 15, 2021 in U.S. Appl. No. 16/648,854.
Final Office Action dated Feb. 25, 2022 in U.S. Appl. No. 16/648,854.
Advisory Action dated May 2, 2022 in U.S. Appl. No. 16/648,854.
Non-Final Office Action dated Jun. 14, 2022 in U.S. Appl. No. 16/648,854.
PCT; International Search Report and Written Opinion dated Dec. 12, 2018 in Application No. PCT/US2018/052166.
PCT; International Preliminary Report on Patentability dated Mar. 24, 2020 in Application No. PCT/US2018/052166.
Non-Final Office Action dated Mar. 16, 2022 in U.S. Appl. No. 16/967,395.
Huh, D et al. "From Three-Dimensional Cell Culture to Organs-on-Chips" Trends Cell Biology, Dec. 7, 2011; vol. 21 Issue 12: pp. 745-754.doi:10.1016/j.tcb.2011.09.005.

(56) References Cited

OTHER PUBLICATIONS

USPTO; Notice of Allowance dated Aug. 3, 2022 in U.S. Appl. No. 16/438,092.
USPTO; Final Office Action dated Sep. 1, 2022 in U.S. Appl. No. 16/967,395.
USPTO; Notice of Allowance dated Sep. 8, 2022 in U.S. Appl. No. 16/648,854.

* cited by examiner

BIOPRINTER AND METHODS OF MANUFACTURING AN ORGANOMIMETIC DEVICE

CROSS REFERENCE TO RELATED APPLICATIONS

This application is a U.S. national stage entry under 35 U.S.C. ʃ371 of International Application No. PCT/US2019/017540 filed Feb. 11, 2019 entitled "BIOPRINTER AND METHODS OF MANUFACTURING AN ORGANOMIMETIC DEVICE," which claims priority to, and the benefit of, U.S. Provisional Patent Application Ser. No. 62/628,727, filed on Feb. 9, 2018, the entire contents of which are incorporated herein by reference in their entirety.

GOVERNMENT LICENSE RIGHTS

This invention was made with government support under grant number HHSF223201810127C awarded by Food and Drug Administration. The government has certain rights in the invention.

FIELD

The present disclosure relates to three-dimensional printing, and more particularly to bioprinters and methods of manufacturing organomimetic devices.

BACKGROUND

Lung diseases are a major global health problem with a rising incidence and morbidity. For example, chronic obstructive pulmonary disease (COPD), which is currently the third leading cause of death in the United States, lacks an effective therapeutic that can reverse, stop, or even mitigate the disease progression. This, in part, has been attributed to our rudimentary understanding of the biogenesis of human diseases and inadequate in vitro and in vivo models. In fact, animal models of human pulmonary disorders, due to considerable inter-species differences with humans, have been largely ineffective in identifying novel drug targets and translating the findings to clinical arena. Additionally, existing in vitro culture models are unable to recapitulate dynamic interaction between the lung structural cells (e.g., epithelium) and innate immune defense (e.g., recruitment and activation of circulating immune cells) in response to pathogenic and non-pathogenic airborne challenges; a process that is crucial to recapitulate when studying lung pathophysiology. Additionally, these static models cannot recreate exposure of lung tissue to aerosolized smoke or inhaled particles under physiologically relevant breathing airflow conditions.

Organ-on-chips are biomimetic, microfluidic, cell culture devices created with microchip manufacturing methods that contain perfused hollow microchannels inhabited by living tissue cells arranged to simulate organ-level physiology. By recapitulating the multicellular architectures, tissue-tissue interfaces, chemical gradients, mechanical cues, and vascular perfusion of the body, these devices produce levels of tissue and organ functionality not possible with conventional 2D or 3D culture systems. They also enable high-resolution, real-time imaging and in vitro analysis of biochemical, genetic, and metabolic activities of living human cells in a functional human tissue and organ context.

SUMMARY

In various embodiments, the present disclosure provides a bioprinter for manufacturing an organomimetic device. The bioprinter may include at least one extruder configured to extrude a material, a three-dimensional movement assembly, and a build-plate mounted to the three-dimensional movement assembly. The build-plate may be configured to support the organomimetic device being manufactured. The bioprinter may further include a controller operably coupled to and configured to control the at least one extruder, the three-dimensional movement assembly, and the build-plate.

The bioprinter may further include a cabinet for housing the at least one extruder, the three-dimensional movement assembly, the build-plate, and the controller. The cabinet may comprise multiple doors to allow access to various components of the bioprinter. In various embodiments, the at least one extruder is non-movably fixed to the cabinet. In various embodiments, the at least one extruder comprises three extruders. Each extruder of the three extruders may be configured to extrude a different material. The extruder(s) may be configured to extrude a biological material, such as a cellular material or an acellular material. In various embodiments, the at least one extruder comprises a thermal regulation system.

In various embodiments, the three-dimensional movement assembly comprises three linear stages: an x-axis stage, a y-axis stage, and a z-axis stage. In various embodiments, the build-plate is mounted to the z-axis stage. The build-plate may comprise a thermal modulation system, and the thermal modulation system may be configured to enable the build-plate to have a temperature above 60 degrees Celsius. In various embodiments, the build-plate includes an anti-crash assembly. In various embodiments, the accuracy and the resolution of the bioprinter is less than 1 micrometer. In various embodiments, the accuracy and the resolution of the bioprinter is about 500 nanometers.

Also disclosed herein, according to various embodiments, is a bioprinter for manufacturing an organomimetic device that includes a cabinet, three extruders, a three-dimensional movement assembly, a build-plate, and a controller. The three extruders may be non-movably mounted within the cabinet, wherein the three extruders are configured to extrude material. The three-dimensional movement assembly may be housed within the cabinet, and the three-dimensional movement assembly may comprise an x-axis stage, a y-axis stage, and a z-axis stage. The build-plate may be mounted to the three-dimensional movement assembly, and the build-plate may be configured to support the organomimetic device being manufactured. The controller, according to various embodiments, is operably coupled to and configured to control the three extruders, the three-dimensional movement assembly, and the build-plate.

Also disclosed herein, according to various embodiments, is a method of manufacturing an organomimetic device. The method may include mounting a chip to a build-plate of a bioprinter, wherein the build-plate is mounted to a three-dimensional movement assembly housed within a cabinet. The method may also include moving, by a controller and via the three-dimensional movement assembly, the build-plate relative to at least one extruder non-movably fixed to the cabinet. Further, the method may include extruding, by the controller and via the at least one extruder, material onto the chip to define an organomimetic device.

The at least one extruder comprises three extruders, wherein extruding material onto the chip comprises each extruder of the three extruders extruding a different material, according to various embodiments. The material may be biological material, such as a cellular material or an acellular material.

The forgoing features and elements may be combined in various combinations without exclusivity, unless otherwise expressly indicated herein. These features and elements, as well as the operation of the disclosed embodiments, will become more apparent in light of the following description and accompanying drawings.

Figure 1A:
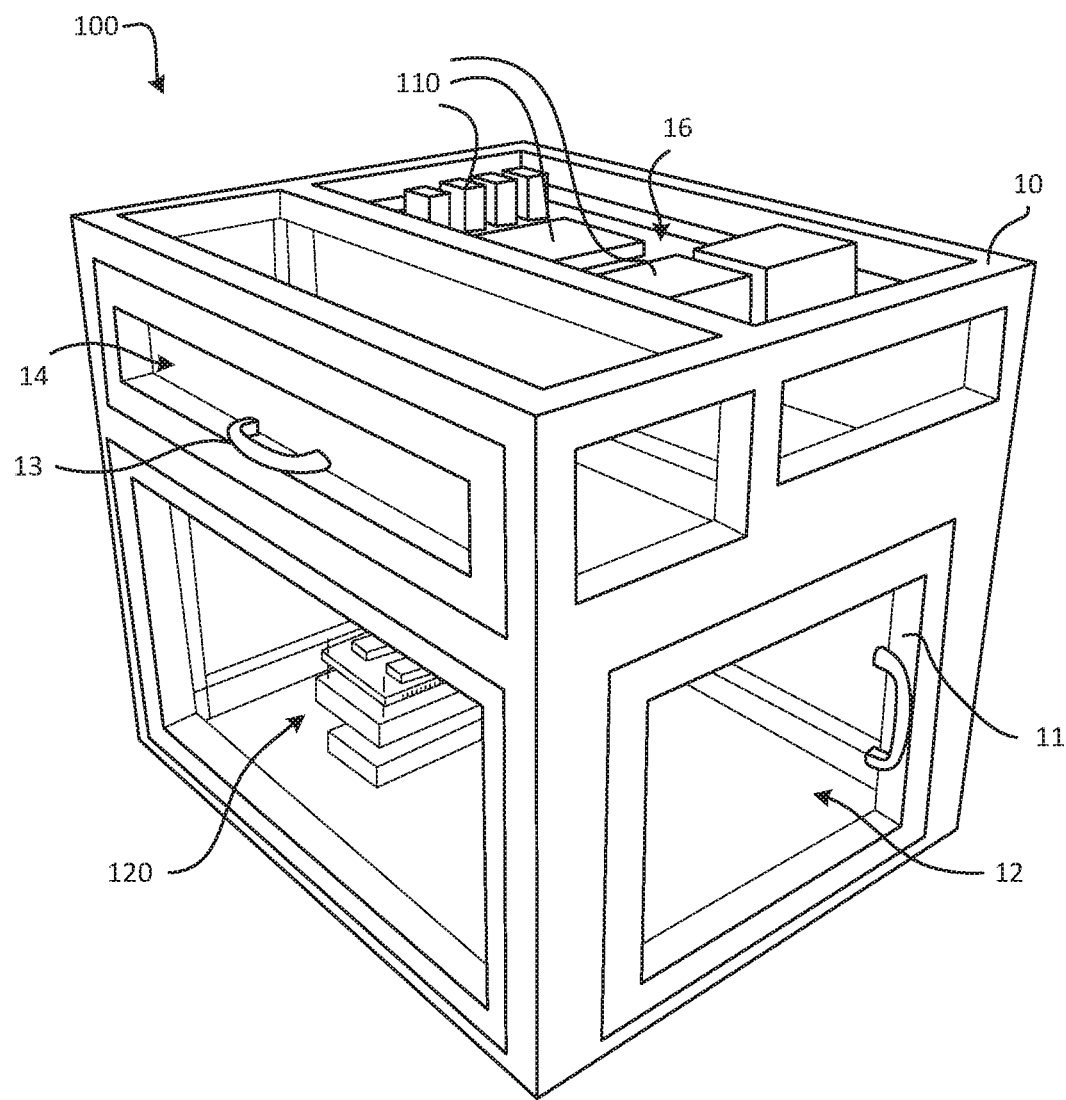
FIG. 1A is a schematic perspective view of a bioprinter for manufacturing organomimetic devices, the bioprinter comprising a cabinet for housing components, in accordance with various embodiments.

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

DETAILED DESCRIPTION

The detailed description of exemplary embodiments herein makes reference to the accompanying drawings, which show exemplary embodiments by way of illustration. Although these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and is not limiting.

Disclosed herein, according to various embodiments, is a bioprinter for and a method of manufacturing an organomimetic device. Generally, the bioprinter may be utilized to manufacture a variety of different organomimetic devices or other bio-devices. As used herein, the term organomimetic device generally refers to an 'organ-on-a-chip' device that generally provides tissue and organ functionality. Although numerous details are included herein pertaining to a lung-on-a-chip implementation, the present disclosure may be applicable to and implemented in conjunction with other organs and/or to provide other physiological functions. Additionally, the bioprinter and method of manufacturing may be utilized to produce devices for organ functionality that provide high-resolution, real-time imaging and in vitro analysis of electromechanical, biochemical, genetic, and metabolic activities of living human cells in a functional human tissue and organ context. In various embodiments, channels and/or lumens of the organomimetic device may be inhabited by various living tissue cells arranged to simulate organ-level physiology. In various embodiments, the organomimetic device is configured to recapitulate multicellular architectures, tissue-tissue interfaces, chemical gradients, mechanical cues, and vascular perfusion of the body. In various embodiments, an organomimetic device may be used in vitro or in vivo. In various embodiments, an organomimetic device may be an implant and thus may be implemented as a replacement organ or may otherwise replace or augment organ functionality of a patient. Further, the organomimetic device provided herein may be used for drug efficacy testing, biomarker discovery, pathogen exposure analysis, drug development, immunologic response testing, and for diagnostic purposes, among others.

Figure 1B:
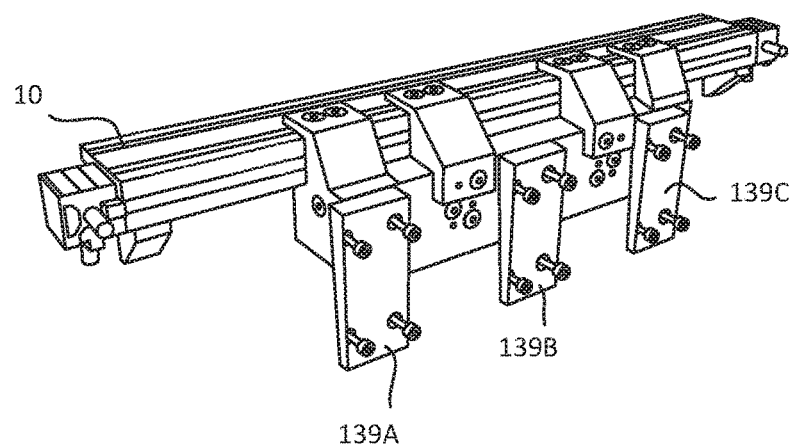
FIG. 1B is a perspective view of an extruder mount bracket of a bioprinter, in accordance with various embodiments.
Figure 1C:
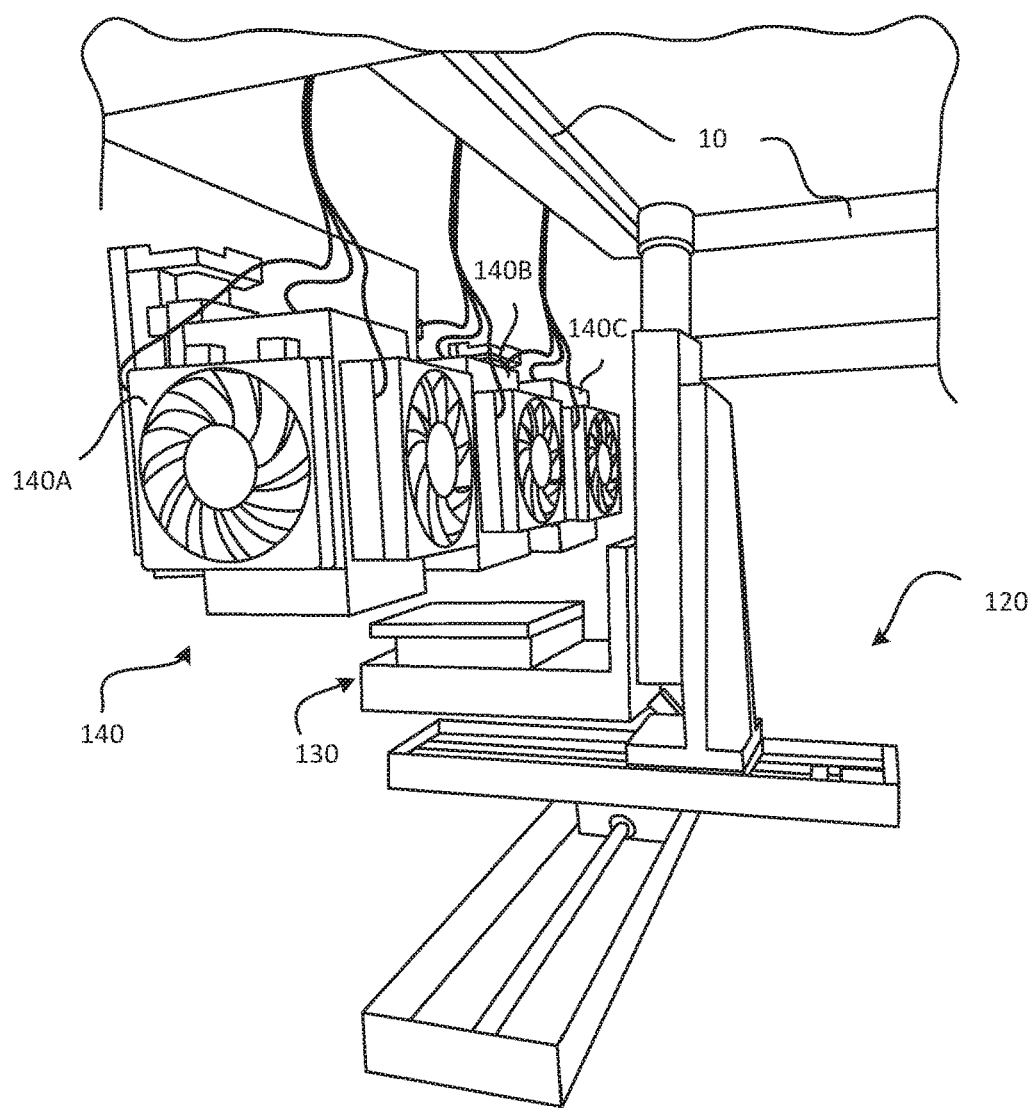
FIG. 1C is a perspective view of a three-dimensional movement assembly, a build-plate, and a plurality of extruders of a bioprinter, in accordance with various embodiments.

In various embodiments, and with reference to FIGS. 1A, 1B, and 1C, a bioprinter 100 is provided. Generally, the bioprinter 100 includes components, features, and functionality that overcome various shortcomings of conventional printing devices and/or organ-on-a-chip devices. For example, the bioprinter 100 may be able to create an organomimetic device that incorporates lung parenchymal cells like fibroblasts between the airway epithelial tissue and the microvascular endothelium to allow the study of fibrotic responses. Further, the bioprinter 100 may enable the presence of a sub-epithelial extracellular matrix (ECM) within the organomimetic device, thereby allowing for analysis of matrix remodeling and immune cell migration through a natural matrix. Still further, the bioprinter 100 disclosed herein may be utilized to improve the shape (e.g., uniform circular shape) of the cross section of the printed airway lumens and vascular channels, thereby improving functional dynamics and resulting in a more representative model of biological systems. Accordingly, the bioprinter 100 contemplated and disclosed herein enables printed organomimetic devices to include sub-epithelial matrix and ECM cellular components in addition to the epithelium and the endothelium, and may include one or more tube-like microchannels for re-creation of small airway lumen and blood microvessels in a precisely printed network.

Additionally, the bioprinter 100 provided herein may be capable of thermally regulating and printing material (referred to herein as "the printed material," the "extruded material," or "the material"). The material may be "fugitive inks," (which are used to create microchannels, as described in greater detail below) and/or various ECM-based hydrogels with high positional and volumetric dispensing accuracy. As explained in greater detail below, the structure and configuration of the bioprinter provides various benefits, such as the ability to print/extrude biological materials (e.g., cellular material and acellular material) to create microfluidic device, according to various embodiments. Further, the structure and configuration of the bioprinter 100 enables operation/printing at an accuracy and resolution of less than 1 micrometer, according to various embodiments. In various embodiments, the accuracy and resolution is about 500 nanometers. Still further, the structure and configuration of the bioprinter 100 allows for printing/extrusion of robust biological materials because the extruders may be non-movably fixed to the cabinet 10, as described below, according to various embodiments. Also, the bioprinter 100 may be configured such that the temperature of the build-plate can reach temperatures beyond 60 degrees Celsius.

In various embodiments, and with reference to FIGS. 1A, 1B, and 1C, the bioprinter 100 comprises a cabinet 10 for housing the various components of the bioprinter 100. The cabinet 10 generally provides the housing, casing, and/or framework for the components of the bioprinter 100. In various embodiments, the bioprinter 100 includes a controller 110, a three-dimensional movement assembly 120, a build-plate 130, and at least one extruder 140, as described in greater detail below. In various embodiments, and with reference to FIG. 1A, the cabinet 10 may define a first compartment 12, a second compartment 14, and a third compartment 16. These compartments 12, 14, 16 may not necessarily be strictly isolated from each other, but may be regions of the cabinet 10 where specific components of the bioprinter are disposed. For example, the first compartment 12 may have a first access door 12 and the three-dimensional movement assembly 120 may be generally disposed therein (see FIG. 1C, which shows a view of the components in the first compartment 12 and the second compartment 14). The second compartment 14 may have a second access door 13 and the extruder assembly may at least be partially disposed therein. The third compartment 16 may house the controller 110. As used herein, the term "controller" 110 generally refers to the components that control operation of the bioprinter 100, as described in greater detail below. Generally, the cabinet 10 houses the devices and peripherals that affect operation of the bioprinter 100, and thus may include electric and/or pneumatic peripherals, conduits, valves, etc.

In various embodiments, the cabinet 10 may be designed to allow for scalability and sterility. In various embodiments, the controller 110 (e.g., electronic and pneumatic control units) may be separate and isolated from the working chamber where the build-plate is located. Accordingly, the printed structure of the organomimetic device may be isolated from everything except the linear stages, the build-plate, and the extrusion assembly. Additionally, the crevasses and other depressions from support brackets and/or other mounting or fastening features may be covered with folded sheet metal, which may result in all inner surfaces exposing only metal walls, glass, and a minimal number of bolts. Accordingly, as mentioned above, the bioprinter 100 may fit within a biosafety cabinet to allow for increased sterility.

In various embodiments, and with specific reference to FIGS. 1B and 1C, the bioprinter 100 may include more than one extruder 140 (e.g., extruders 140A, 140B, and 140C). As described in greater detail below, the extruder(s) is not attached to the linear actuator slides, according to various embodiments, and thus there are fewer, if any, weight restrictions on the extrusion assembly, thus allowing more for the bioprinter 100 to include more than one extruder 140 without increasing the load on the movement/translation assembly. For example, the extrusion assembly may support two or three extruders (or more) per build-plate 120. The extruders 140A, 140B, 140C may be mounted to the frame of the cabinet 10 via an extruder mount bracket (FIG. 1B). The extruder mount bracket may have interfaces 139A, 139B, and 139C to which the extruders 140A, 140B, and 140C are mounted.

Figure 2:
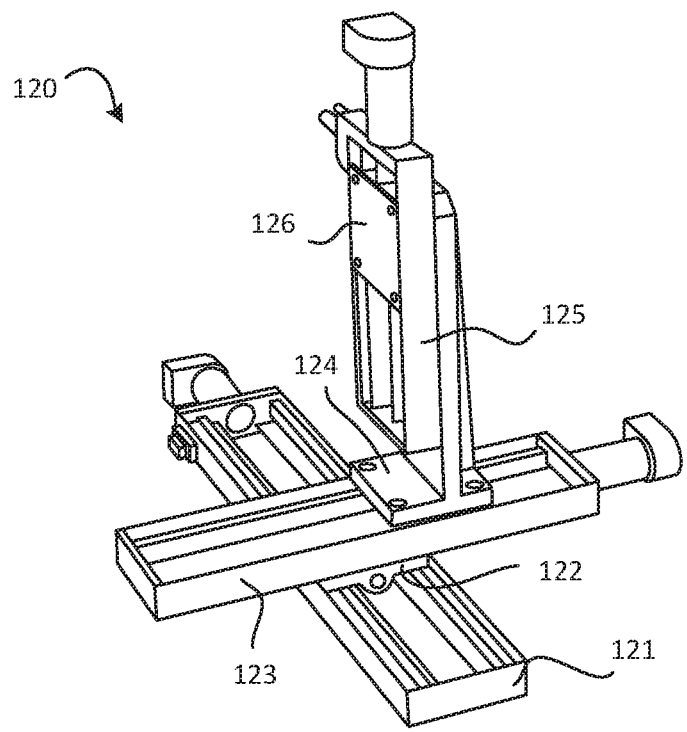
FIG. 2 is a perspective view of a three-dimensional movement assembly of a bioprinter, with the three-dimensional movement assembly comprising three linear stages, in accordance with various embodiments.

In various embodiments, and with reference to FIG. 2, the three-dimensional movement assembly 120 includes three linear stages: an x-axis stage 121, a y-axis stage 123, and a z-axis stage 125. Corresponding carriages 122, 124, 126 may be configured to move along respective linear stages 121, 123, 125. The build-plate 130 may be mounted to the z-axis stage 125 at carriage 126. The linear stages may have various stroke lengths according to the dimensions and overall configuration of the bioprinter 100. For example, the x, y, and z linear stages may have 300-, 200-, and 100-millimeter stroke lengths, respectively. Stroke length defines the end-to-end travel distance of the carriage (the part that moves on each linear stage). The build-volume of the bioprinter 100 may be dependent on these stroke lengths, and the three dimensional movement assembly 120 of the bioprinter 100 may allow for multiple extruders to be used, thereby enabling and enhancing the capability of the bioprinter to use bioinks of various thermal and viscous properties simultaneously.

In various embodiments, the three dimensional movement assembly 120 enables high design resolution printing, high unidirectional repeatability (e.g., extremely low levels of deviation from 500 nanometer resolution of printing during repeating seeks), low angular crosstalk error (e.g., low error in parallelism between the top face of the carriage as it actuates and the bottom face of the linear stage), high maximum velocity (e.g., 20 millimeters per second), and high load capacity (e.g., around 50 Newton (N) or more). Additionally, the three-dimensional movement assembly 120 may provide additional key features, such as a direct current motor with a rotary encoder, which generates positional closed loop feedback systems which allows a user to identify the precise location of the carriage at any desired time during printing and improves positional accuracy by the machine. The three-dimensional movement assembly 120 may also include embedded mechanical limit switches that enhance precision for homing of the build-plate. Still further, the linear stages of the three-dimensional movement assembly 120 may be made from anodized aluminum or other such material, which may improve sterility during operation. The linear stages may be electric stages and the linear slides may be pneumatic, electric, or hydraulic.

In various embodiments, and with reference to FIGS. 1A, 1B, 1C, 2, 3, 4A, and 4B, the three-dimensional movement assembly 120 may be utilized to move the build-plate 130 relative to the extruders 140. Because the extruder is not being moved by the linear stages of the movement assembly, potentially less weight is required to be moved around within the bioprinter 100 compartment and thus less force, stress, and strain is imparted to the linear stages even when adding additional extruders to the bioprinter 100.

Figure 3:
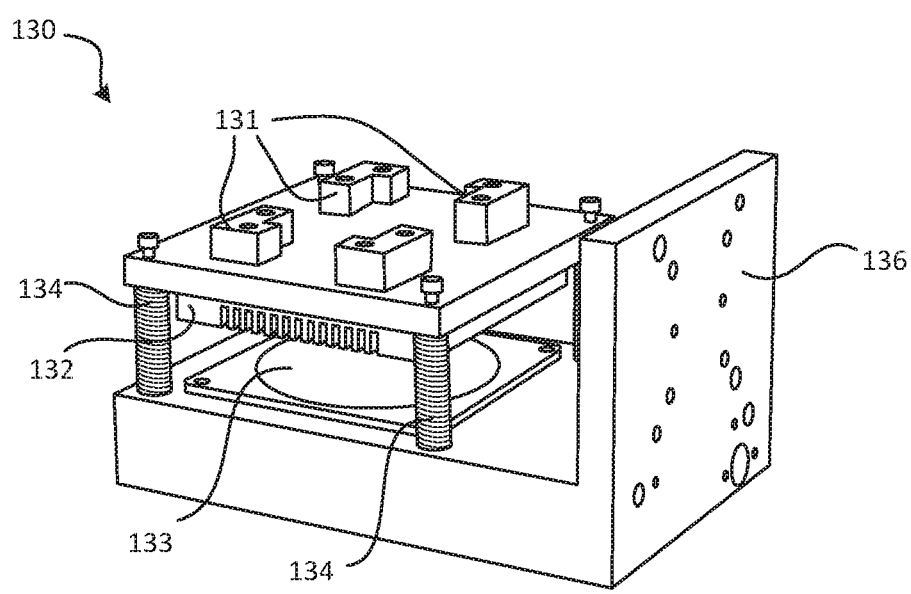
FIG. 3 is a perspective view of a build-plate of a bioprinter, in accordance with various embodiments.

In various embodiments, and with reference to FIG. 3, the build-plate 130 is the component of the bioprinter 100 upon which the organomimetic device will be printed. That is, a chip (e.g., a biochip) may be coupled to the build-plate 130 using retention elements 131. The retention elements 131 may be adjustable so as to accommodate different sizes. The build-plate 130 may include a thermal modulation system. The thermal modulation system may include a thermoelectric heater-cooler, a heat sink 132, and/or fan 133. The heater-cooler may be a solid-state active heat pump that uses the Peltier effect to heat or cool the environment immediately surrounding the bio-block, thereby allowing the user to accurately control polymerization and de-polymerization of the printed bioinks. The build-plate 130 may include an anti-crash support assembly 134 that protects against accidental damage caused by inadvertent or undesired movements. The anti-crash support assembly 134 may provide force damping, for example through a spring-based system. The build-plate 130 may also incorporate manual or automated leveling of the bed of the build-plate 130.

In various embodiments, the build-plate may also include a high-precision contact sensor that provides real-time location feedback on the extruder position to the control software during operation. In various embodiments, the bioprinter may also include datum locator functionality for bed leveling (e.g., a method for measuring build-plate corner elevation to provide feedback into bed leveling) and location sensing of the extruders either independently or combined into a single system. Such a configuration allows for high precision parallelism measurements and adjustments of the bed. Bed-leveling functionality may be accomplished using an algorithm to inform user of precise adjustments for bed leveling screw adjustments.

In various embodiments, the bioprinter 100 may include an additional build-plate. For example, a second build-plate may be oriented anti-parallel to first build-plate in the Y axis (perpendicular to extruder mounting bracket). This configuration involves additional extruders mounted on the oppose wall of the initial extruder assembly in order to print on the second build-plate. In various embodiments, the bioprinter may enable additional positional calibration of the additional extruder in response to using two independent sets of extruder systems. This allows for the relative positional deviations in extruders within an extruder assembly to be identical between the two. The functionality of the bioprinter may also include high precision location and/or logging of extruder nozzles, as described in greater detail below.

In various embodiments, the controller 110 (FIG. 1) may include pneumatics, translation controllers, and/or other hardware for controlling the extrusion, movement, and other functionality of the bioprinter 100. The bioprinter 100 may include a user control interface to enable user control. In various embodiments, the control assembly may be linked (via I/O pins, wirelessly, etc.) to control software or may be otherwise subjected to control via a remote controller (desktop computer, laptop computer, mobile device application, etc.). For example, the control assembly may have low level integration with operating systems through dynamic linked libraries. The control assembly may enable synchronization of movements between the pneumatics and the linear stage carriages and may have the capability to load in custom databases that include physical parameters of linear stages and variables related to the feedback and control mechanisms, thereby promoting high-precision printing. The control assembly may enable real-time and synchronous operation and control.

Figure 4A:
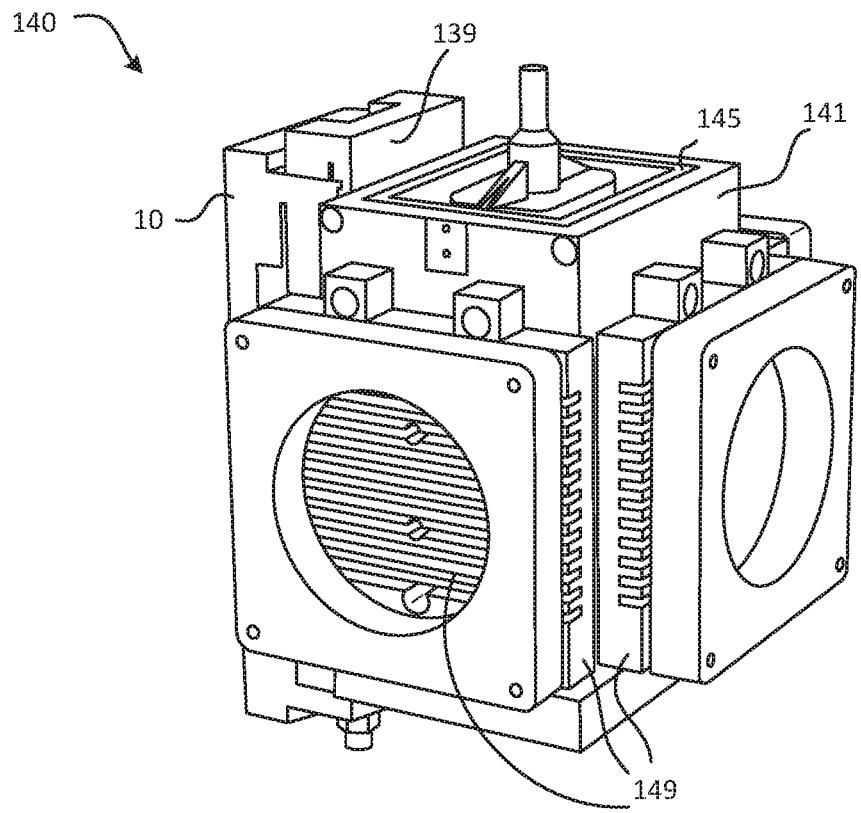
FIG. 4A is a perspective view of an extruder of a bioprinter, in accordance with various embodiments.
Figure 4B:
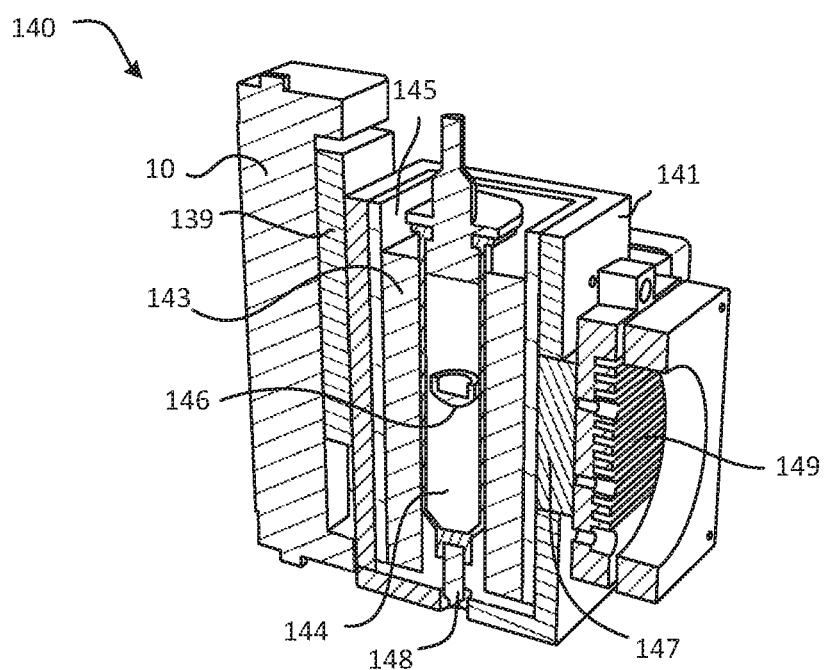
FIG. 4B is a cross-sectional view of an extruder of a bioprinter, in accordance with various embodiments.

In various embodiments, and with reference to FIGS. 4A and 4B, the extruder 140 may be generally configured to extrude/print material (e.g., bioinks) onto the build-plate. The extruder 140 may have an outer housing 141, and the outer housing 141 may be connected to a respective mounting interface 139 of the extruder mount bracket. In various embodiments, each extruder may be selectively and individually lowered and raised depending on which extruder is in-use. For example, the extruders that are not being used may be elevated away from the three-dimensional movement assembly 120 to prevent crashes/collisions. The extruder 140 may include a pneumatically, hydraulically, or electrically controlled actuator to control extrusion/printing. In various embodiments, the extruder 140 may include a syringe 144 with a piston 146 disposed therein. Movement of the piston 146 within the syringe 144 may be in response to vacuum/pressure modulation, which in turn causes material to be extruded through the needle 148 and onto the build-plate.

The extruder 140 may include one or more thermoelectric heater-coolers to thermally regulate the temperature of material/bioinks during the extrusion process. For example, the extruder 140 may include a coupler 147 and a heat sink 149, with the coupler 147 facilitating selective heat transfer through the outer casing 141 and to the heat sink 149. The thermal regulation system of the extruder 140 may consists of three Peltier heat pumps wired in series and attaches to three of the side faces of the extruder 140. The inner casing 143, within which the syringe 144, rests may be heated or cooled within a range of 0 degrees Celsius to 80 degrees Celsius. When the syringe 144 is being cooled, heat is generated on the other side of the Peltier which contacts the heat sink coupler, which transfers the heat to the heat sink and is dissipated by the heat sink fans. In order to improve the thermal isolation of the extruder system, the inner casing block and the outer case are thermally isolated through a sheet of aerogel. In various embodiments, the extruder 140 may include a pen-syringe insulation system, which is a double-paned system intended to further enhance thermal isolation of the bioink from the environment to prevent unanticipated polymerization or de-polymerization of the extruded material. In various embodiments, for example, the extruder 140 may include a layer of insulation 145 disposed between the outer casing 141 and an inner casing 143.

In various embodiments, each extruder 140 may include a pneumatic-powered syringe to controllably extrude the bioink. In various embodiments, the extruder 140 may be electrically or hydraulically actuated (e.g., instead of pneumatically actuated). The extruder may also have additional capacity to retract the bioink under vacuum during idle times to prevent unwanted dripping. Further, the extrusion assembly may include a multi-way valve (either a manually or automatically actuated valve) to switch between printing and refilling modes, and/or to enable multiple different types of bioink to be changed out. In various embodiments, the bioprinter may be configured to allow the extrusion assembly to be swapped out for a different mechanism (e.g., an imaging mechanism or photonic crosslinking mechanism, among others) to aid and facilitate the manufacture of organomimetic devices. In various embodiments, the bioprinter may include a UV crosslinking light source (attached to the build-plate or to the extruder assembly) that facilitates the printing and curing process. The extrusion assembly may be responsive and operable over a dynamic pressure range to support printing of materials with a dynamic viscosity range.

Figure 5:
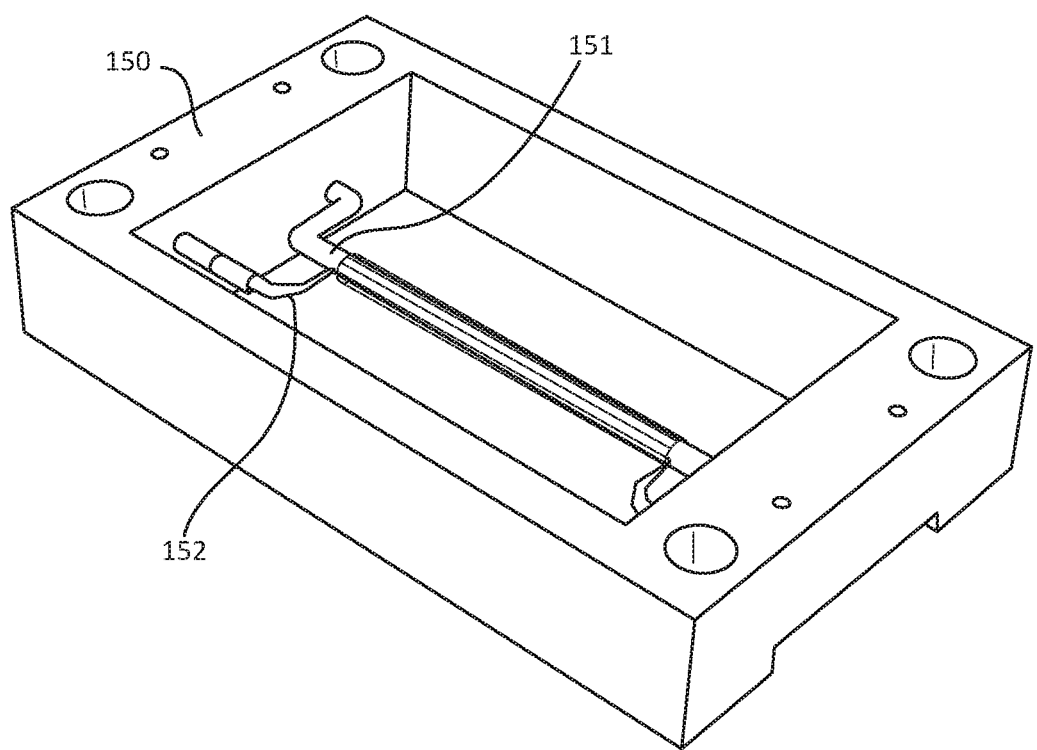
FIG. 5 is a perspective view of an organomimetic device, in accordance with various embodiments.

In various embodiments, and with reference to FIG. 5, an exemplary organomimetic device 150 is provided. The organomimetic device may include multiple types of fluid channels, such as an airway channel 151 and a vascular channel 152. For example, the airway channel 151 may be a lung airway and one or more vascular blood vessel channels 152 may extend along adjacent to the lung airway. As stated above, whereas numerous details are included herein pertaining to a lung-on-a-chip implementation, the present disclosure may be applicable to and implemented in conjunction with other organs and/or to provide other physiological functions. The different (e.g., first and second types of channels) may be separated from each other and surrounded by an extracellular matrix.

In various embodiments, the bioprinter 100 is designed to print multiple materials through a coaxial needle, which may improve the circular shape (e.g., decrease eccentricity) of the extruded material and the resultant microchannel, while providing a native ECM environment to allow for cell migration and matrix remodeling. Printing low eccentricity microchannels may be accomplished because of the thermal polymerization properties of the fugitive inks and the ECM based hydrogels. That is, fugitive inks may solidify above 4 degrees Celsius and may be liquid below 4 degrees Celsius, whereas the hydrogels may be solid to semi-solid below 37 degrees Celsius and may be liquid above 37 degrees Celsius. Accordingly, when both materials are printed in tandem through a coaxial extruder of the bioprinter, large thermal exchanges from the materials after printing may cause the bioinks to solidify rapidly, thus improving circular geometric fidelity.

In various embodiments, the bioprinter may support printing biomaterials of different viscosities at micro-scale resolution and at desired temperatures. Additionally, the bioprinter may be able to print bio-scaffolds having desired dimensions (e.g., that exceed 1 cm in thickness). In various embodiments, the entire bioprinter system may be small enough to fit in a regular laminar flow biosafety cabinet for sterile printing.

Figure 6:
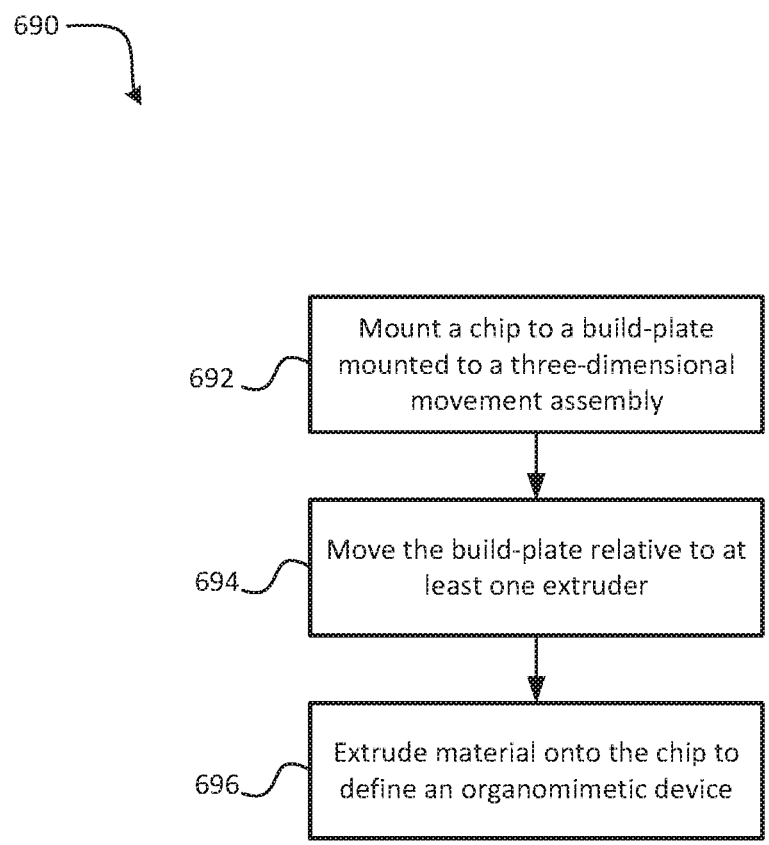
FIG. 6 is a schematic flow chart diagram of a method of manufacturing a organomimetic device, in accordance with various embodiments.

In various embodiments, and with reference to FIG. 6, a method 690 of manufacturing an organomimetic device is provided. The method 90 may include mounting a chip to a build-plate of a bioprinter at step 692. The build-plate may be mounted to a three-dimensional movement assembly housed within a cabinet. The method 90 may also include moving, by a controller and via the three-dimensional movement assembly, the build-plate relative to at least one extruder non-movably fixed to the cabinet at step 694. Further, the method 690 may include extruding, by the controller and via the at least one extruder, material onto the chip to define an organomimetic device at step 696.

The at least one extruder may comprise three extruders, wherein extruding material onto the chip comprises each extruder of the three extruders extruding a different material, according to various embodiments. The material may be biological material, such as a cellular material or an acellular material.

In various embodiments, the method 690 may further include fabricating microfluidic inlets and outlets, which allow for insertion of 19-gauge needles or the like (based on desired channel geometry), for the ECM scaffold that will be printed during the next step. One set of inlet-outlet pair will serve as connection point for culture medium for the vascular network and another set that will provide culture medium to the airway microchannel while cells are still submerged (pre-air-liquid interface), according to various embodiments. In various embodiments, the perfusion chip of the organomimetic device will have a glass undersurface to enable microscopic analyses, and rigid side walls made from Styrene Ethylene Butylene Styrene (SEBS), a form of thermoplastic elastomer with styrene added, or polycarbonate to ensure maximal protection of the ECM-printed materials and ease of handling.

In various embodiments, the method 690 may include manufacturing a cellular or acellular scaffold using the bioprinter by using needles with appropriate diameter. The method may include (1) printing a fugitive bioink, such as pluronic F-127 mixture with thrombin, or the like, within the 3D microfluidic perfusion chip mentioned above. The fugitive bioink may be used to print a plurality of vascular channels (for example, 12 blood vessel channels) that are circumferentially distributed around a central airway lumen. Similarly, an airway lumen using fugitive bioink can be printed. The dimension/diameter of the lumen can be user defined to simulate naturally occurring dimensions/diameters. For example, the lumens may be small airways with a radius of 1 millimeter or less, or larger conducting airways with a greater diameter. In various embodiments, a maximum of 1 millimeter distance may be between adjacent microvasculature channels. The fugitive ink is a material that ultimately is removed under mild conditions by thermally induced de-crosslinking to create hollow tube-like channels, according to various embodiments. Pluronic F-127, for example, is stiff and solid-like at 37° C. but de-polymerizes at 4° C., which allows it to be gently washed out by cold medium. The method may further include (2) casting an ECM material, which contains gelatin, fibrinogen and/or transglutaminase, among others, over the printed bioink. Following casting, according to various embodiments, thrombin diffuses out into the ECM and induces fibrinogen cleavage and rapid polymerization into fibrin. At the same time, transglutaminase slowly crosslinks the gelatin and fibrin into a solid gel. The method may further include (3) evacuating the fugitive ink by either cooling down the whole system or via gentle passage of 4° C. medium. Such a step will leave behind a pervasive vascular network as well as an airway lumen, as shown and described above with reference to FIGS. 6A, 6B, and 6C. In various embodiments, the method may also include (4) cell culture and perfusion.

In various embodiments, the microchannels to-print for this platform will have a radius of 1,000 μm and 50 μm for the airway and the microvascular lumens, respectively. Moreover, the ECM thickness underneath the airway lumen will be engineered at 3 mm to enable microscopic analysis of cilia beating and secretory function of the epithelium. In various embodiments, the cell culture and perfusion step may include seeding primary healthy human small airway epithelial cells at $2.5 \times 10^5$ cells per square centimeter in the central (airway) microchannel in a Small Airway Epithelial Cell Growth medium ("SAECG" medium). This step may further include allowing the seeded material to attach (3-6 hours) and expand (3-7 days) before the fluid in the airway channel is replaced with air, creating an air-liquid interface to promote ciliated differentiation. At the time of seeding, the printed block may be rotated 45 degrees at 10-15 min intervals to ensure that the whole inner surface of the airway lumen is covered with the cells. The epithelium may be cultured for about 3-5 weeks to induce mucociliary differentiation. During this process, the culture may be fed continuously through the blood vessel network. Afterwards, primary human lung microvascular endothelial cells (HMVEC-L; Lonza; after magnetically separating out LYVE-1-psotive lymphatic cells) may be seeded at $4 \times 10^5$ cells per square centimeter by flowing adequate volume of cell suspension through the chip's vascular microchannels so that it fills up the network. Similar to epithelial cell seeding, the device with be rotated at 45 degrees every 10-15 min to allow endothelial cell adhesion throughout the inner surface of the microvascular network. Microvascular Endothelial Growth Medium 2 (EGM-2MV, such as Lonza) may be used for seeding. The devices will be then connected to peristaltic pump for flow for 3 days to allow tight endothelial monolayer formation. Next, primary human lung fibroblasts (PromoCell, Lonza), that are transfected with eGFP to enable microscopic visualization, may be added atop the gelatin gel and allowed to penetrate in the ECM (within 1-2 days). At the same time, monocyte-derived macrophages (MCMs) generated from peripheral blood mononuclear cells (PBMCs) may be added apically at $2.5 \times 10^3$ cells per square centimeter to the airway channel, allowed to adhere to the mucociliated epithelium by incubation at 37° C. for 2 hours, and then unattached cells will be removed. At this point, chips we will be ready for experimentation (e.g., inhalation exposure to respiratory pathogens or tobacco smoke). The cell seeding sequence, densities and choice of culture media can all be optimized and adjusted based on the needs of the user.

In various embodiments, the steps of printing and casting may be repeated, interchanged, omitted, or otherwise modified based on the needs of the specific biodevice being manufactured. As mentioned above, pluronic fugitive inks may be used together with hydrogels during the printing and/or casting steps.

In various embodiments, the bioprinter 100 may include internal UV lights to disinfect the bioprinter and its components. In various embodiments, the build-plate 130 includes embedded UV lights for sterilization. For example, each corner of the build-plate 130 may have an embedded UV light. The bioprinter 100 may include holes, perforations, or apertures to enable a vacuum to be drawn within one or more compartments defined by the bioprinter casing/housing. In various embodiments, the bioprinter 100 may include an ambient air cooling and heating system to improve the thermal regulation of the printed structure (i.e., the organomimetic device), which may reduce clogging at the tip of the extruder nozzle. In various embodiments, the bioprinter 100 may support utilization of 12 gauge to 32 gauge needle inserts (coaxial or non-coaxial) or the like, and may include the following functionalities: non-sequential layer deposition, deposition of material into layers, printing above current/existing layers, and the formation of low eccentricity microchannels via coaxial printing.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A bioprinter for manufacturing an organomimetic device, the bioprinter comprising:
   at least one extruder;
   a three-dimensional movement assembly;
   a build-plate wherein the build-plate comprises a UV crosslinking light source; and
   a controller configured to control the at least one extruder, the three-dimensional movement assembly, and the build-plate.

2. The bioprinter of claim 1, wherein the at least one extruder comprises a multi-way valve the multi-way valve having a first position and a second position, the first position for printing and the second position to for refilling the at least one extruder.

3. The bioprinter of claim 1, wherein the at least one extruder comprises a UV crosslinking light source.

4. The bioprinter of claim 1, wherein the at least one extruder is configured to extrude a material and Wherein the material comprises a first material and a second material printed in tandem wherein the first material solidifies above 4 degrees Celsius and is liquid below 4 degrees Celsius and the second material is a solid to semi-solid below 37 degrees Celsius and a liquid above 37 degrees Celsius.

5. The bioprinter of claim 1, wherein the at least one extruder comprises a first extruder and a second extruder and the first extruder and second extruder are coaxial.

6. The bioprinter of claim 1, wherein the at least one extruder is non-movably fixed to a cabinet and the bioprinter further comprising holes, perforations, or apertures to enable a vacuum to be drawn within one or more compartments defined by the cabinet.

7. The bioprinter of claim 6, wherein the cabinet comprises a first compartment, a second compartment, and a third compartment, the first compartment comprising a first access door and the three-dimensional movement assembly is disposed in the first compartment, the second compartment comprises a second access door and the at least one extruder is disposed in the second compartment and the controller is disposed in the third compartment.

8. The bioprinter of claim 1, wherein the three-dimensional movement assembly comprises three linear stages: an x-axis stage, a y-axis stage, and a z-axis stage and the x-axis stage comprises an x-axis carriage, the y-axis stage comprises a y-axis carriage, and the z-axis stage comprises a z-axis carriage and the x-axis carriage is configured to move the z-axis carriage Wherein the x-axis stage has a 300 millimeter stroke length, the y-axis stage has a 200 millimeter stroke length, and the z-axis stage has a 100 millimeter stroke length.

9. The bioprinter of claim 8, wherein the stroke lengths define the end-to-end travel distance of the x-axis carriage, y-axis carriage and z-axis carriage.

10. The bioprinter of claim 1, wherein the three-dimensional movement assembly comprises an embedded mechanical limit switch.

11. The bioprinter of claim 1, wherein the at least one extruder is mounted to a cabinet via a mounting bracket and further comprising a second build-plate oriented perpendicular to the at least one extruder mounting bracket.

12. The bioprinter of claim 1, wherein the build-plate is moveable relative to the at least one extruder and the at least one extruder is moveable relative to the build-plate.

13. A bioprinter for manufacturing an organomimetic device, the bioprinter comprising:
    at least one extruder;
    a three-dimensional movement assembly; and
    a build-plate wherein the build-plate comprises a UV crosslinking light source at each of the build-plate's four corners.

14. A bioprinter for manufacturing an organomimetic device, the bioprinter comprising:
    at least one first extruder;
    a three-dimensional movement assembly;
    a first build-late and a second build-plate oriented antiparallel to the first build-plate in the axis; and
    a controller configured to control the at least one first extruder, the three-dimensional movement assembly, the first build-plate and the second build-plate.

15. The bioprinter of claim 14, wherein the at least one first extruder is mounted to a first wall of a cabinet and further comprising a second extruder mounted to a second wall of the cabinet wherein the first wall and second wall are opposite each other.

16. The bioprinter of claim 6, wherein the second extruder and the at least one first extruder are two independent extruder systems.

17. The bioprinter of claim 15, wherein when the second extruder is lowered the at least one first extruder is raised.

* * * * *